United States Patent
Lundy et al.

(10) Patent No.: US 7,976,867 B2
(45) Date of Patent: Jul. 12, 2011

(54) DERMAL, TRANSDERMAL, MUCOSAL OR TRANSMUCOSAL INGREDIENT DELIVERY DEVICES

(75) Inventors: Charles E. Lundy, Germantown, TN (US); Gary Wynn Cleary, Los Altos Hills, CA (US); Adrian Louis Faasse, Carmel Valley, CA (US); Michael George Marcoux, Wyoming, MI (US); Sreenivasu Mudumba, Union City, CA (US)

(73) Assignees: Schering-Plough Healthcare Products Inc., Memphis, TN (US); Corium International, Redwood, CA (US)

( * ) Notice: Subject to any disclaimer, the term of this patent is extended or adjusted under 35 U.S.C. 154(b) by 1329 days.

(21) Appl. No.: 10/735,318

(22) Filed: Dec. 12, 2003

(65) Prior Publication Data

US 2004/0166147 A1    Aug. 26, 2004

Related U.S. Application Data

(60) Provisional application No. 60/433,203, filed on Dec. 13, 2002.

(51) Int. Cl.
- *A61K 9/70* (2006.01)
- *A61L 15/16* (2006.01)
- *A61F 13/02* (2006.01)

(52) U.S. Cl. ........ 424/449; 424/443; 424/444; 424/447; 424/448

(58) Field of Classification Search .................. 424/448, 424/449
See application file for complete search history.

(56) References Cited

U.S. PATENT DOCUMENTS

| | | | |
|---|---|---|---|
| 2,561,071 A | 7/1951 | Prisk | |
| 2,579,403 A | 12/1951 | Slomowitz et al. | |
| 4,624,665 A | 11/1986 | Nuwayser | |
| 4,743,249 A | 5/1988 | Loveland | |
| 4,863,738 A | 9/1989 | Taskovich | |
| 4,863,970 A | 9/1989 | Patel et al. | |
| 4,877,618 A | 10/1989 | Reed, Jr. | |
| 4,973,468 A * | 11/1990 | Chiang et al. | 424/449 |
| 5,053,227 A | 10/1991 | Chiang et al. | |
| 5,141,750 A | 8/1992 | Lee et al. | |
| 5,234,690 A | 8/1993 | Chiang et al. | |
| 5,254,346 A | 10/1993 | Tucker et al. | |
| 5,342,623 A | 8/1994 | Enscore et al. | |
| 5,462,745 A | 10/1995 | Enscore et al. | |
| 5,641,504 A | 6/1997 | Lee et al. | |
| 5,641,507 A | 6/1997 | Devillez | 424/443 |
| 5,662,925 A | 9/1997 | Ebert | 424/447 |
| 5,770,220 A | 6/1998 | Meconi et al. | |

(Continued)

FOREIGN PATENT DOCUMENTS

WO    96/19205    *    6/1996

(Continued)

*Primary Examiner* — Humera N Sheikh
(74) *Attorney, Agent, or Firm* — Matthew J. Golden

(57) ABSTRACT

A dermal, transdermal, mucosal or transmucosal delivery device is provided. The device includes a backing layer, defining an ingredient containing reservoir, a cover for the reservoir having at least one opening therethrough, an adhesive layer and a liner layer. Upon removal of the liner layer, the device may be placed over the desired area of the skin or mucosa and adhesively applied thereto allowing the ingredients to flow from the reservoir through the at least one opening to the dermis or mucosa.

12 Claims, 3 Drawing Sheets

U.S. PATENT DOCUMENTS

| | | | |
|---|---|---|---|
| 5,788,983 A | 8/1998 | Chien et al. | |
| 5,902,598 A | 5/1999 | Chen et al. | |
| 5,916,587 A * | 6/1999 | Min et al. | 424/448 |
| 5,962,011 A | 10/1999 | DeVillez | 424/488 |
| 5,985,860 A * | 11/1999 | Toppo | |
| 6,004,578 A | 12/1999 | Lee et al. | |
| 6,231,885 B1 * | 5/2001 | Carrara | |

FOREIGN PATENT DOCUMENTS

| | | |
|---|---|---|
| WO | WO 96/19205 | 6/1996 |
| WO | WO96/19205 | 6/1996 |
| WO | WO 99/47128 | 9/1999 |
| WO | 01/26637 * | 4/2001 |
| WO | WO 01/26637 | 4/2001 |

* cited by examiner

DERMAL, TRANSDERMAL, MUCOSAL OR TRANSMUCOSAL INGREDIENT DELIVERY DEVICES

CROSS-REFERENCE TO RELATED APPLICATIONS

This application claims the benefit U.S. Provisional Patent Application No. 60/433,203, filed Dec. 13, 2002, the disclosure of which is hereby incorporated by reference in its entirety.

BACKGROUND OF THE INVENTION

The present invention relates generally to dermal, transdermal, mucosal or transmucosal ingredient delivery devices. Such devices are designed to deliver ingredients to the skin or exposed mucosa of a subject. The device is referred to "dermal" or "transdermal," as a function of whether or not the ingredients are formulated in such a way as to remain on the user's skin and be active there, or pass through the skin. The same distinction applies with respect to "mucosal" or "transmucosal" devices, but with reference to an exposed mucosal layer.

The ingredients to be delivered may vary widely. They may be "drug" ingredients, oral care ingredients such as flavors, drugs, etc., or they could be cosmetic ingredients such as perfumes, creams or the like. The term "active" ingredient as used herein is intended to refer to the primary ingredient or ingredients to be delivered by the device, and is not intended to be used in its "FDA" sense as referring only to "drugs."

Devices for transdermal or percutaneous drug delivery and devices are typically characterized by delivering an amount of a drug or other ingredients, e.g., nitroglycerin, estrogen, estradiol, corticoid, levonorgestrel, etc. to the patient's skin at a rate controlled by the device. In a transdermal or transmucosal device, the drug is delivered systemically to the intended site of treatment within the body. Although effective for their intended use, such controlled release devices have limited utility for providing the kind of treatment which requires maximum delivery of the drug or active ingredient for local skin conditions, for example, lesions or abnormal skin features such as corns, warts, calluses, bunions, actinic keratoses and hard hyperkeratotic skin as is often found on the face, arms, legs or feet.

U.S. Pat. No. 4,849,224 to Chang et al. discloses an ingredient delivery device comprising a backing layer which defines an ingredient containing reservoir covering a microporous membrane that is permeable to the ingredients contained in the reservoir. The microporous membrane is heat sealed to the backing layer in the area surrounding the perimeter of the reservoir. An adhesive layer is adhered to the backing layer in the area surrounding the mircoporous membrane. A release liner covering both the adhesive layer and the microporous membrane is heat sealed to the backing layer concentric to and outwardly from the heat seal between the microporous membrane and the backing layer. In a second embodiment, Chang '224 discloses a similar arrangement, but with a peel sealable inner liner which underlies the microporous membrane and portions of the backing film. It is the inner liner, rather than the release liner, which is then heat sealed to the backing layer with a peelable heat seal which is concentric with the heat seal between the microporous membrane and the backing layer. In this device, both the release liner and the inner liner must be removed prior to application of the device to a patient.

Chang et al. U.S. Pat. No. 4,983,395 discloses a device which is similar to the second embodiment of the Chang '224 patent, except that 1) the membrane layer underlies some or all of the backing layer, 2) the inner liner, membrane and backing layer are all sealed together at the perimeter of the reservoir, and 3) the inner liner is adhered by an adhesive layer to the release liner.

Other types of delivery devices such as medicated plasters have been used for corns, warts, calluses, etc. However, the amount of active ingredient that can be delivered by such plasters is limited by the dimensions of the plaster and solubility of the active ingredient in the plaster. Consequently, repetitive applications are required for effective treatment. It would be desirable to provide a device which would provide maximum delivery of dermatological ingredients for local skin conditions or therapeutic drugs for delivery to the bloodstream.

SUMMARY OF THE INVENTION

The ingredient delivery device of the present invention comprises a backing layer, sometimes referred to herein as a base member, defining an ingredient containing reservoir, and a cover for the reservoir which is made of a material substantially impermeable to ingredients to be contained in the reservoir, but having at least one opening therein such that ingredients will flow readily through the opening but will not readily flow through the material of which the cover is made. The cover is sealed to the backing member at the perimeter of the reservoir by a first seal which is not subject to degradation by any ingredient to be contained in the reservoir. An adhesive layer is adhered to the backing layer for adhering the device to a patient's skin or mucosa. The adhesive layer does not extend to the perimeter of the opening in the cover, such that a portion of the cover surrounding the perimeter is exposed and thereby provides a cover sealing surface. A liner, preferably a release liner for the device, covers the sealing surface of the cover and is releasably sealed to the sealing surface by a second seal which is also not subject to degradation by any ingredient to be contained in the reservoir. The ingredients contained in the reservoir are thereby sealed therein during storage and nonuse by the first and second seals, the cover and the liner, but are free to flow through the opening in the cover and onto a patient's skin or mucosa when the liner is removed from the device and the device is applied to the skin or mucosa.

These and other features, objects and advantages of the invention will be more fully understood and appreciated by reference to the written description and appended drawings.

Figure 1:
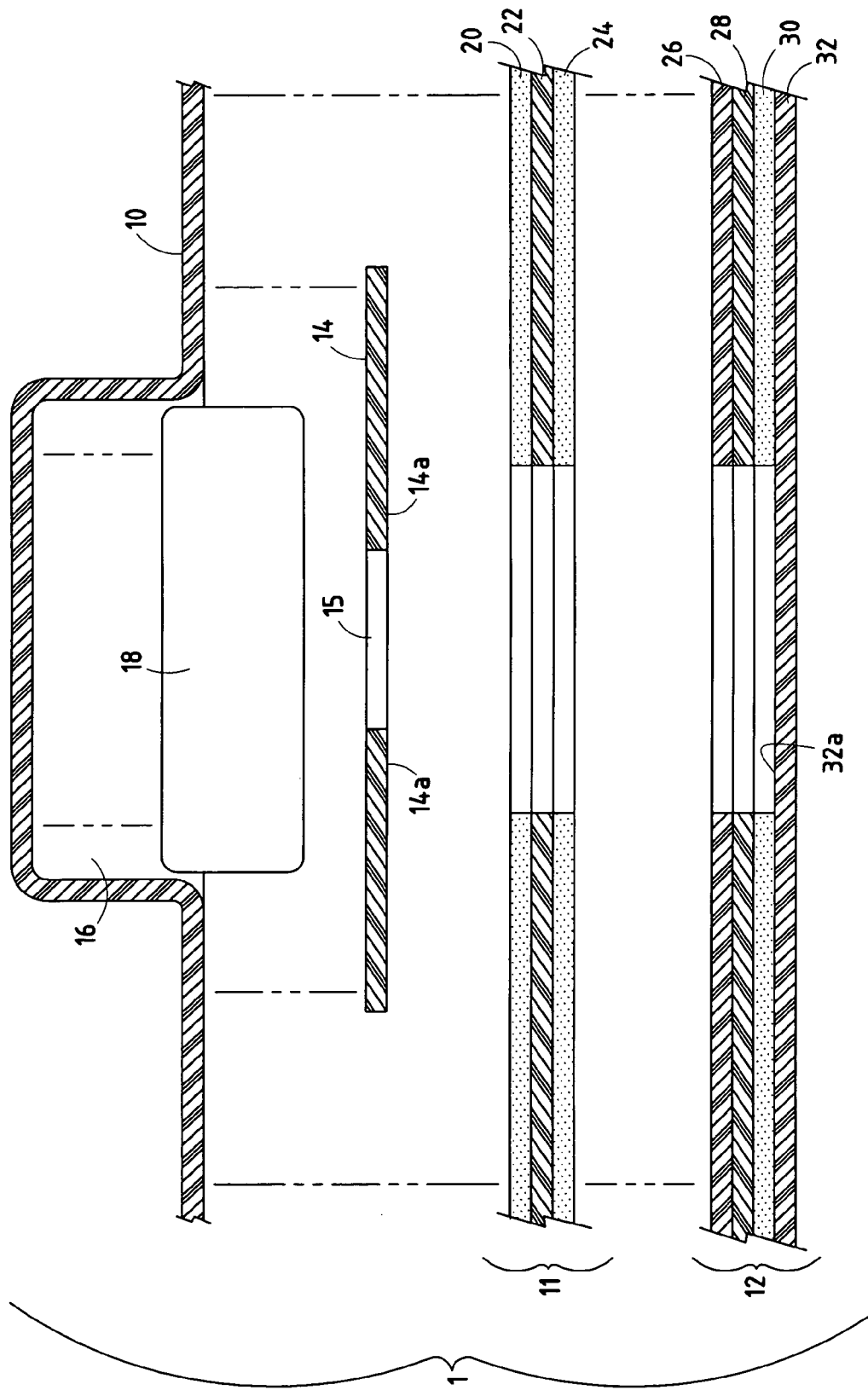
FIG. 1 is an exploded cross-sectional view of the principle subassemblies of the device of the preferred embodiment.

It will be appreciated that the thicknesses and shapes for the various layers have been exaggerated in the drawings to facilitate understanding of the device. The drawings are not "to scale."

DETAILED DESCRIPTION OF PREFERRED EMBODIMENTS

Figure 2:
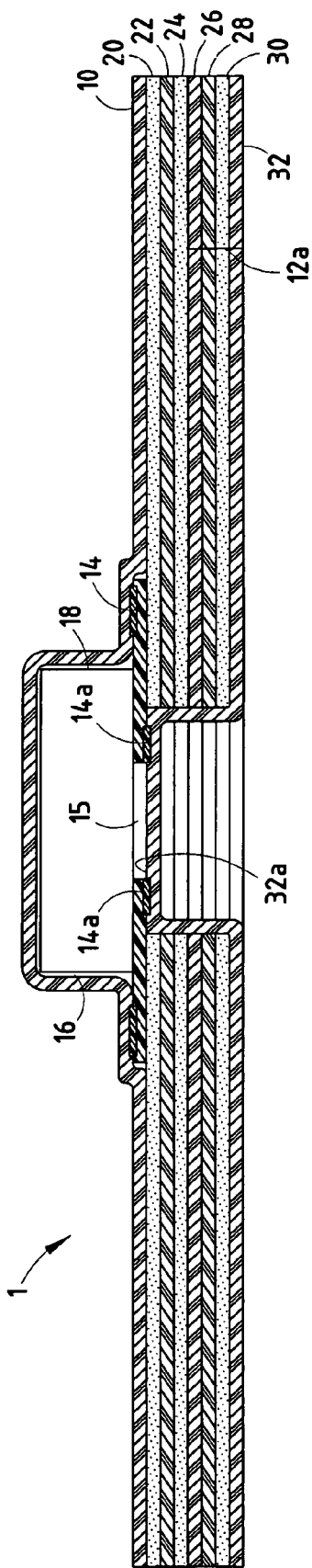
FIG. 2 is an exploded cross-sectional view, showing portions of the major subcomponents of the device of the preferred embodiment.

In the preferred embodiment, device 1 comprises a backing layer (sometimes referred to as a base member) 10 defining a reservoir 16 for containing an ingredient or ingredients 18 (FIGS. 1 and 2). A cover 14 having an opening 15 therein is sealed to backing member 10 around the periphery of reservoir 16 by a seal which is not subject to degradation by ingredients to be contained in reservoir 16. Adhesive layer 11 is adhered to backing member 10 and serves to adhere the device to a patient's skin or mucosa. Adhesive layer 11 may cover a portion of cover 14, but does not cover opening 15, and preferably leaves a portion of the surface of cover 14 exposed in the area surrounding opening 15, the area being referred to herein as cover sealing surface 14A. Liner 12 covers at least opening 15 and sealing surface 14A of cover 14, and is sealed to sealing surface by a second seal which is not subject to degradation by any ingredient to be contained in the reservoir. Preferably, liner 12 comprises the release liner for the device, and therefore covers not only opening 15 and sealing surface 14A, but also releasably covers adhesive layer 11. When device 1 is to be used, release liner 12 is removed, thereby exposing opening 15. Device 1 is then applied to the patient's skin or mucosa via adhesive layer 11, with reservoir 16 and cover opening 15 positioned over the area to which ingredients 18 are to be delivered.

Backing layer or base member 10 is made of a material which is substantially impermeable to ingredients 18, for example, 3.0 mil, 3M® 9722 polyethylene film. Ring-shaped cover 14 is also made of a material which is substantially impermeable to ingredients 18 contained in reservoir 16, for example, 4.0 mil ROLLPRINT® polyethylene film that forms a reservoir 16.

The size or diameter of opening 15 may vary, as a function of the speed with which one wants to deliver active ingredients, or the total amount of active ingredient one wants to deliver from reservoir 16. Depending on intended use, the diameter of opening 15 may range from 0.05 to 5.0 inch. The larger openings would require the use of hydrogel in the reservoir, so the ingredient solution does not immediately run out of reservoir 16 when liner 12 is removed. In the preferred embodiment as shown, the diameter of the opening is approximately 0.125 inches.

Ingredients 18 may be contained within reservoir 16 in any of a variety of ways. For example, ingredients 18 can simply be in liquid form within reservoir 16. The ingredients may be contained in a pad of hydrogel material, which basically comprises a gel matrix containing ingredients to be delivered through opening 15. Alternatively, ingredients 18 may be contained in a woven or non-woven absorbable material pad located in reservoir 16, made of, for example, 5.0 mil STRA-TEX® 90% polypropylene/10% non-woven rayon. Other suitable materials for the absorbable woven or non-woven material include any non-dimensionally stable materials, such as woven polyester cloth, bonded nylon fibers, cotton gauze, fiberglass, polyester fibers and cotton fibers. This material may partially or completely contain the ingredient or ingredients to be delivered to the user's skin or mucosa.

The term ingredient or ingredients as used herein refers to all ingredients contained within reservoir 16, and not only to those of the ingredients which are to be delivered to or through the user's skin or mucosa. The latter may be referred to as "active" ingredients in the broadest sense. However, the term "active" ingredient is not intended to limit the ingredients to be delivered to drugs, since other types of ingredients may be delivered for purposes other than to serve as a drug.

Adhesive layer 11 is preferably a composite of three different layers (FIG. 2) as follows: first or upper adhesive layer 20, made of, for example, a 1.0 mil, NATIONAL STARCH 80-1197™ acrylic adhesive; barrier layer 22, made of, for example, a layer of 0.5 mil, PET film; and second or lower adhesive layer 24, made of, for example, 3.0 mil, NATIONAL STARCH 80-1197™ acrylic adhesive that comes into contact with the patient's skin. Other suitable materials for attaching the device 10 to the skin or mucosa can include waterproof tape or other materials that have an adhesive underside. Pressure sensitive adhesive is preferred. The adhesive may be resistant to permeation and/or dissolution by the ingredients in reservoir 16, but this is not essential in view of the first and second seals discussed above. Other suitable adhesives may include but are not limited to the following: A. Solvent-based acrylic adhesives such as: Monsanto GMS 737, trademark of Monsanto Corporation, St. Louis, Mo.; National Starch Durotak 72-9720 and 80-1197, trademark of National Starch & Chemical Corp., Bridgewater, N.J.; Ashland's AROSET 11 13-AD-40 and 1085-A-45, trademark of Ashland Oil Co., Ashland, Ky.; B. Solvent-based rubber adhesives such as: National Starch 36-6172; C. Acrylic emulsion adhesives such as: Monsanto GME 2397 Rohm & Haas N580, trademark of Rohm & Haas Co., Philadelphia, Pa.; Unocal 76 RES 9646, trademark of Unocal Corp., Los Angeles, Calif.; and Ashland's AROSET 2022-W-50. C. Adhesive Transfer Tapes such as: 3M F-9465 PC, trademark of 2M Co., St. Paul, Minn. Avery-Denison MED 1116, trademark of Avery Dennison Corp., Pasedena, Calif.; ARCare 7530, trademark of Adhesive Research Inc., Glen Rock, Pa.; and RX230U, trademark of Coating Science Inc., Bloomfield, Conn.

The upper and lower adhesive layers 20 and 24 are both adhered to the intermediate barrier layer 22. Adhesive layer 20, in turn, is adhered to backing member 10, and also partially to cover 14, but does not extend beyond and over the sealing surface 14A of cover 14.

Release liner 12 also preferably is comprised of a plurality of layers of material as follows: release coating layer 26 made of, for example, LOPAREX® (REXAM®) 92A release coating; barrier layer 28 made of, for example, 3.0 mil, PET film; adhesive layer 30, made of, for example, 1.0 mil NATIONAL STARCH 80-1197™ acrylic adhesive; and outer protective layer 32, which is a co-laminated film of polyamide and polyolefins layer, made of, for example, TOLAS™ 4050.

Release coating layer 26 is bonded to barrier layer 28. Adhesive layer 30 is bonded to the other side of barrier layer 28, and to outer protective layer 32. This entire assembly of layers functions as a unitary release liner.

As best seen in FIG. 2, release coating layer 26, barrier layer 28 and adhesive layer 30 preferably have openings which are coextensive with the opening left in adhesive layer 11. In other words, layers 26, 28 and 30 of release liner 12 only partially overlie cover 14, and leave sealing surface 14A and opening 15 exposed. Outer protective layer 32, on the other hand, has no such opening and entirely covers sealing surface 14A and opening 15 of cover 14. Thus it is preferably the exposed inner surface portion 32A of outer protective layer 32 which is sealed to sealing surface 14A of cover 14 by the previously referred to second seal which is not subject to degradation by any ingredient to be contained in reservoir 16.

While those skilled in the art could probably select adhesives for the first and second seals which would not be degradable by the particular ingredients to be contained in reservoir 16, the first and second seals are preferably heat seals. Thus, cover 14 is preferably heat sealed to backing layer 10 in the area thereof surrounding reservoir 16, and outer layer 32 of release liner 12 is preferably heat sealed in area 32A to sealing surface 14A. The materials and sealing conditions used to seal area 32A to sealing surface 14A are preferably such that this second seal is "releasable" when force is applied to remove release liner 12 from adhesive composite 11. In contrast, the first seal between cover 14 and backing layer 10 should be "permanent" to the extent that cover 14 is not peeled away from backing layer 10 when a force is applied to remove release liner 12 from the assembly.

The preferred embodiment device may also include a shell covering the exterior of reservoir 16. The shell of the device should be impermeable or impervious to the liquid being delivered to the treatment site, in order to prevent loss by evaporation or wetting. The shell may also protect the active ingredient and/or liquid against radiant energy sources such as ultraviolet and visible light. The shell can be either dimensionally stable or dimensionally non-stable, preferably dimensionally non-stable. A dimensionally non-stable shell is not capable of withstanding a compressive force of one psi or less, i.e. will at least partially crush or collapse. Suitable materials for the shell can include but are not limited to ceramics, metals such as titanium, aluminum or steel, plastics such as polyolefins, barex, styrene, polyesters, polyacrylics, vinyl polymers, polyamides, polyfluorocarbons, polyimides, polylactams, polyaramides, polycarbonates, polysulfones, polyethylene, polypropylene, nylon, polyvinyl chloride or composites thereof. It will be appreciated that the shell could replace the reservoir defining portion of the film of material comprising backing layer 10. In that case, the reader should consider the shell to be a part of backing layer 10 for purposes of this discussion. The shell would then be the portion of backing layer 10 defining reservoir 16 for containing the ingredients to be delivered. Reservoir 16 of the device is a structure having sufficient interior surface area to retain the ingredients against a gravitational force by means of surface energy to prevent the liquid from readily draining out of the reservoir. The reservoir can be either dimensionally stable or dimensionally non-stable, as discussed above. The heat seal around reservoir 16 should also be resistant to permeation, disintegration or degradation e.g., dissolving by the ingredients and actives contained herein.

Figure 4:
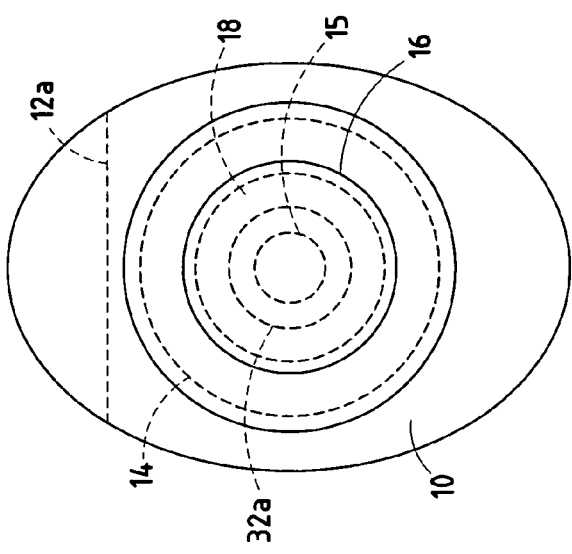
FIG. 4 is a similar plan view of an alternative embodiment device having a somewhat different configuration from the device of FIGS. 1-3.
Figure 3:
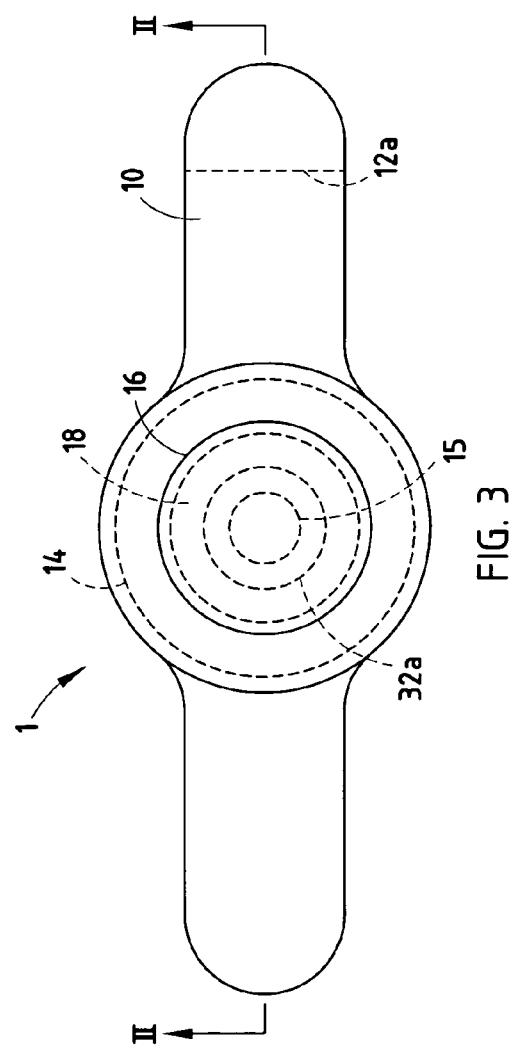
FIG. 3 is a plan view of the device of FIGS. 1 and 2, showing the device which is applied to a patient's skin or mucosa.

Turning to FIG. 3 which is a plan view of the device of the present invention, there is an opening 15 in cover 14 for release of the medication to the patient's skin from the reservoir 16 that contains thin absorbable ingredient containing woven or non-woven layer 18, which, in turn, is contained within the cover 14 that is sealed to backing layer 10. A kiss cut line 12a is present in release liner 12 to aid in removing the disposable release liner 12. FIG. 4 is an alternative shape of the object of the present invention.

Preferred embodiment device 1 delivers active ingredients at high concentrations over short periods of time (i.e. ranging from about 0.1 hour to about 24 hours per wear). Some active ingredients at lower concentrations may be delivered for more than about 24 hours. The preferred embodiment device 1 is useful for delivering active ingredients in liquid solution without adding or incorporating an adhesive film (i.e. with no layer between the skin and the liquid containing the active ingredient) into the preferred embodiment device 1. Preferred embodiment device 1 may be used to treat the following conditions or to deliver the following active ingredients, the conditions and active ingredients including, but not limited to: warts (i.e. salicylic acid, and/or other keratolytic agents); acne (i.e. salicylic acid, benzoyl peroxide, antibiotics, and/or other keratolytic agents); pain (i.e. local anesthetics, non-steroidal anti-inflammatory drugs); moisturizers (i.e. urea, water); finger and toenail beds (i.e. urea, water, anti-fungal agents); skin buffering (i.e. buffering agents); vaccines (i.e. small pox, measles, flu, anthrax, polio, etc.); poorly soluble drugs; larger molecular weight molecules (i.e. about 500 to about 1500 molecular weight molecules such as heparin, LHRH); wound care (i.e. water, debriding agent(s), enzymes); sampling and diagnostic agents (i.e. glucose, lactic acid, potassium, allergens, etc.); iontophoresis, electroporation, sonophoresis, radio frequency, thermal enhancement (reservoir) (i.e. electrode (anode, cathode)); microneedles (reservoir) (i.e. alone or in combination with iontophoresis, electroporation, sonophoresis, radio frequency, thermal enhancement). The preferred embodiment device 1 may also be combined with other components, deliver other active ingredients, and/or deliver molecule(s) for diagnostic purposes to the skin.

Preferred embodiment device 1 was tested using an organic keratolytic agent solution which is basically non-aqueous not withstanding trace amounts of water. Such keratolytic agents include salicylic acid or salts or esters thereof, glacial acetic acid, glycolic acid, phenoxyacetic acid, ascorbic acid, retinoic acid (tretinoin), fluorouracil, calcium pantothenate, cantharidin, podophyllum, phenol, zinc chloride, tannic acid, castor oil, or mixtures thereof. The amount of active ingredient in the liquid can range from about 1 to about 40% by weight, preferably from about 5 to about 30%, most preferably 20% by weight. Most preferably, the active ingredient is salicylic acid or a salt or ester thereof. Suitable salts include the sodium, potassium, calcium or magnesium salts thereof. Suitable esters include $C_1$ to $C_4$ esters thereof, such as methyl salicylate. Other esters include salsalate (salicylsalicylic acid), the salicylate ester of salicylic acid. Salicylic acid was used in the examples below.

Salicylic acid has a history of safe use for the treatment of a variety of skin conditions. The topical uses of salicylic acid under the OTC monographs considered to be safe and effective are: a topical acne treatment (21 CFR 333.310; at 0.5-2%); the removal of warts (21 CFR 358.110) when used in a plaster vehicle (12-40%), in a collodion-like vehicle (5-17%) or in a karaya gum, glycol vehicle (15%); the removal of calluses and corns (21 CFR 358.510) when used in a plaster vehicle (12-40%) or in a collodion-like vehicle (12-17.6%); and the control of dandruff, seborrheic dermatitis and psoriasis (21 CFR 358.710; at 1.8-3%).

Salicylic acid produces desquamation of the horny layer of skin while not affecting the structure of the viable epidermis by dissolving intercellular cement substance. The keratolytic action causes the cornified epithelium to swell, soften, macerate and then desquamate. (Drug Facts and Comparisons, 2000).

The organic solution described below has been shown to enhance the mobility of salicylic acid through the skin as can be seen from flux measurements on cadaver skin shown in FIG. 5 as set forth below. The organic solution provides an improved vehicle for salicylic acid and/or other medicaments, which promotes the removal of warts, corns, calluses, and other keratolytic skin lesions.

The medicated devices of this embodiment, containing this solution, overcome problems existing with currently available medicated pads because the rate and extent of transfer of salicylic acid from the device across the stratum corneum is much faster than the rate of and extent of salicylic acid transfer in other commercially available solutions as demonstrated below in FIG. 5. The medicated devices of this embodiment deliver topically at the site of the wart, corn, or callus, thereby avoiding any significant systemic absorption.

Furthermore, the organic solution has a low volatility at ambient temperatures. Previous formulas showing high flux (transfer rates) of salicylic acid across the skin were composed of lower molecular weight, more volatile solutions that are difficult to contain. Therefore the described salicylic acid solution has the advantage of being more stable and having a longer shelf-life than previous formulas. The organic solution is described in more detail below.

One component of the organic solution is a solvent composed of compounds such as $C_2$-$C_9$ alkylene diols, e.g., butylene diol, pentylene glycol, neopentyl diol, propylene glycol being preferred. Also included solvents are such as diethylene glycol, monoethyl ether or like compounds such as Di $C_2$-$C_5$ alkylene dio, mono $C_1$-$C_4$ alkyl ethers, e.g., dipropylene glycol, mono propyl ether, polypropylene glycol and co-polymers, mono poropy ether, polyethylene glycol, mono ethyl ether. Suitable surfactants for the organic solution include, for example, monoglycerides or like compounds such as glyceryl mono-oleate, -laurate, -behenate, -eicosadioate, -sterate, or other fatty acid mono substituted glycerides. Suitable film formers for the organic solution include, for example, polyacrylamide or other like compounds which act as thickening agents such as other acrylamide copolymers, polyacrylate copolymers, cellulosic polymers and copolymers, and poly vinyl pyrolidone polymers and copolymers.

The device can be applied to cover the wart, corn or callus for an appropriate time period, such as for example, 4 to 24 hours, or optionally it may be removed after 8-10 hours of treatment. Alternatively, the device can be applied to cover the wart, removed after 8-10 hours of treatment, after which the procedure can be repeated.

The following is the listing of ingredients of keratolytic treating solution discussed above.

| Ingredient | Trade or Other Name |
|---|---|
| Salicylic Acid USP | 2-Hydroxylbenzoic acid |
| Diethylene Glycol Monoethyl Ether NF | Transcutol ® P |
| Propylene Glycol USP | 1,2-Propanediol |
| Glyceryl monooleate NF | glycerol monooleate, Peceol |
| Sepigel 305 | Polyacrylamide and $C_{13-14}$ isoparaffin and laureth-7 |

The salicylic acid is present as an active ingredient. The Propylene Glycol USP, Monoglycerides NF and Diethylene Glycol Monoethyl Ether NF are present as solvents. The Sepigel 305 is present as a viscosity modifier. The salicylic acid is preferably in an amount of 125 mg/patch. Preferably, the ingredients are present in the following amount by weight of ingredient per formulation.

| Ingredient | (% w/w) |
|---|---|
| Salicylic Acid USP | 20 |
| Diethylene Glycol Monoethyl Ether NF | 10 |
| Propylene Glycol USP | 48 |
| Glyceryl monooleate NF | 20 |
| Sepigel 305 | 2 |

The following procedure is representative of the manufacturing process for the bulk Salicylic Acid Topical Solution 20% drug product. Into a suitable vessel equipped with a propeller mixer, add Propylene Glycol. Begin mixing. With continued mixing (400 rpm); add Sepiegel 305 and mix until an essentially clear viscous material is produced (2-4 hours). Add Diethylene Glycol Monoethyl Ether; mix until uniform (1 hour). Add Glycerol Monooleate and mix until dissolved (1 hour). The solution will be hazy. Add Salicylic Acid slowly over 2 hours and continue to mix for 4 hours. The product will be a viscous, clear solution (less viscous than after step 2).

FIGS. 1 and 2 show the layers of materials used to manufacture the preferred embodiment device 1. The layers of materials that may be used in the manufacture of the device are listed below. Generally, the preferred embodiment device 1 includes a backing layer 10, an adhesive layer 11 and a release liner 12.

The following is a description of from the backing layer to the release liner (top to bottom on FIGS. 1 and 2) by layer number and description:

10. Backing layer, i.e. 3.0 ml, 3M® 9722 polyethylene film;
18. Reservoir ingredients, i.e. 5.0 mil STRATEX® 90% polypropylene/10% non-woven rayon;
14. Cover, i.e. 4.0 mil ROLLPOINT® polyethylene film;
11. Adhesive layer
20. First adhesive coating, i.e. 1.0 mil National Starch 80-1197 acrylic adhesive
22. Barrier layer, i.e. 0.5 mil PET film; and
24. Second adhesive coating, i.e. 3.0 mil National Starch 80-1197 acrylic adhesive;
12. Release liner;
26. Release coating layer, i.e. LOPAREX® (REXAM®) 92A release coating;
28. Barrier layer, i.e. 3.0 mil PET film;
30. Adhesive coating, i.e. 1.0 mil NATIONAL STARCH 80-1197™; and
32. Outer protective layer, i.e. TOLAS™ 4050;

Any commercially known method of manufacturing the preferred embodiment device 1 may be employed. However, one preferred method of producing device 1 includes the following steps: 1) pre-cut the materials used in the backing 10 and the reservoir layer 16 (i.e, pre-cut cover 14 and any woven and/or non-woven ingredients); 2) peel away the strip layers from first adhesive layer 10 and second adhesive layer 24 and adhere the skin contact adhesive layer 11 to the release liner 12; 3) place cover 14 in position on completed step 2 assembly, heat seal cover 14 to the outer protective layer 32 and set aside; 4) form reservoir 16 in the backing material; 5) place ingredients 18 in the formed reservoir, insert any active ingredient(s), place completed step 3 assembly in position over reservoir 16 and heat seal backing 10 to cover 14; 6) die cut finished shape; 7) inspect for defects and contamination; and 8) place the finished device 1 in a pouch and seal the pouch.

The following examples were carried out in accordance with the above procedures. The following formulations were placed in the reservoirs 16 of devices made in accordance with embodiment 1.

| Percent | Ingredient |
|---|---|
| FORMULA 1 | |
| 20% | Salicylic acid |
| 32% | Ethanol |
| 40% | Propylene glycol |
| 8% | Water |

| Percent | Ingredient |
|---------|-----------|
| \multicolumn{2}{c}{FORMULA 2} | |
| 20% | Salicylic acid |
| 10% | Diethylene glycol monoether |
| 20% | Glyceryl monooleate |
| 48% | Propylene glycol |
| 2% | Polyacrylamide in a parafinic mixture with laureth-7 |

Figure 5:
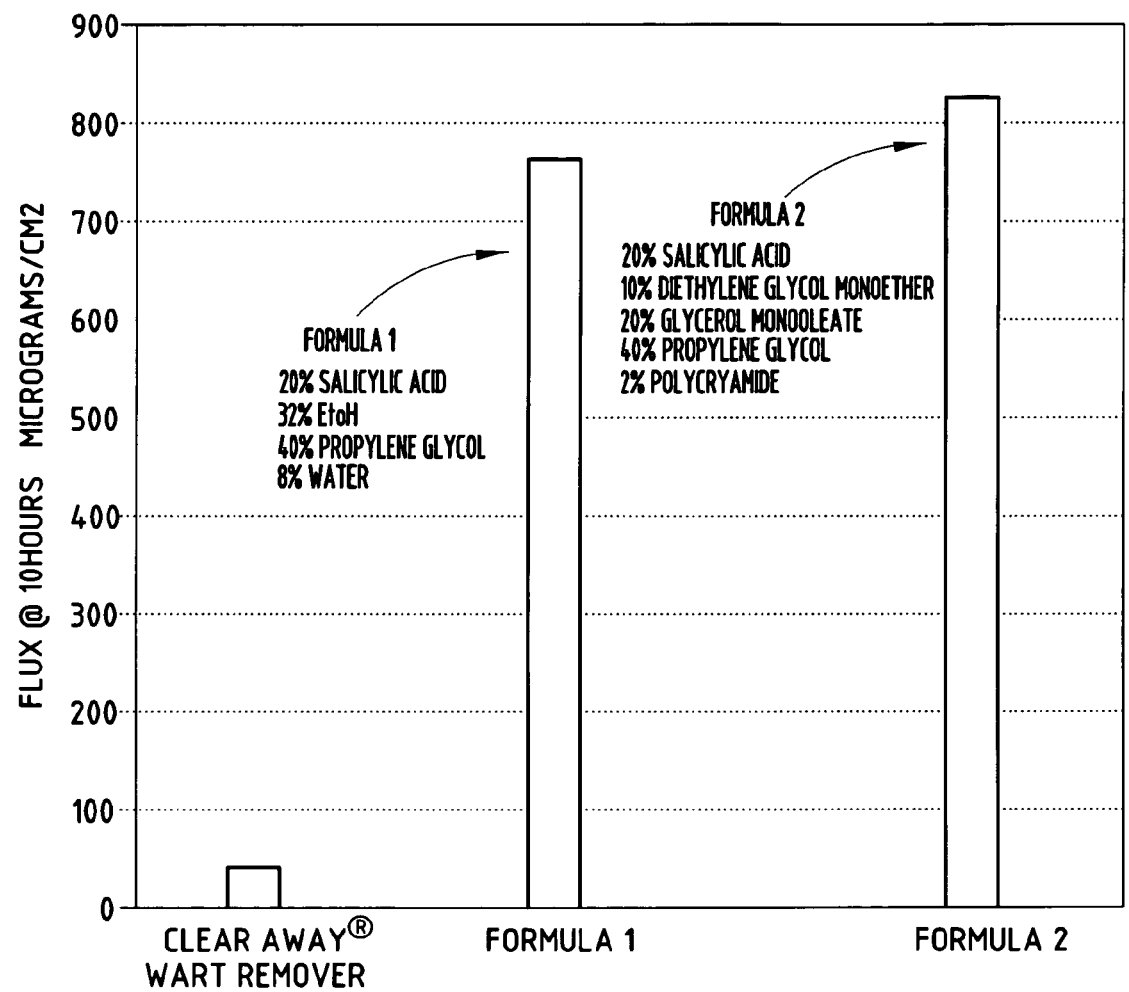
FIG. 5 is a chart displaying a comparison of flux in salicylic acid formulas contained in devices of the preferred embodiment to medicated plasters in the prior art.

The flux in salicylic acid for Formulas 1 and 2 dispensed in a device made in accordance with preferred embodiment device 1 were compared as shown in FIG. 5 to the flux achieved using Clear Away® wart remover of the prior art. Flux was compared to 10 hours at micrograms absorbed by $cm^2$. As can be seen, the Clear Away® wart remover of the prior art had less than 50 micrograms absorbed/$cm^2$. The devices of preferred embodiment 1 using formulas greater than nearly 700 and 800 $cm^2$, respectively.

Having described specific preferred embodiments of the invention with reference to the accompanying drawings, it will be appreciated that the present invention is not limited to those precise embodiments and that various changes and modifications can be effected herein by one of ordinary skill in the art without departing from the scope or spirit of the invention as defined by the appended claims.

What is claimed is:

1. An ingredient delivery device, comprising:
    a backing member defining an ingredient containing reservoir, said backing member being made of a material which is substantially impermeable to ingredients contained in said reservoir;
    an ingredient contained in said reservoir comprising an organic solution, wherein said organic solution comprises:
        a topically active drug agent;
        an alkylene glycol;
        a fatty acid ester;
        a dialkylene glycol alkyl ether; and
        a polymeric thickening agent;
    a cover for said reservoir, said cover being made of a material substantially impermeable to ingredients contained in said reservoir, but having at least one opening therein, such that ingredients to be delivered from said reservoir will flow through said opening, but will not readily flow through said material of which said cover is made;
    said cover being sealed to said backing member at the perimeter of said reservoir by a first seal which is not subject to degradation by any ingredient to be contained in said reservoir;
    an adhesive layer adhered to said backing member for adhering said device to a patient's skin or mucosa, said adhesive layer not extending to the perimeter of said opening in said cover, such that a portion of said cover surrounding said perimeter of said opening is exposed to thereby define a cover sealing surface; and
    a unitary release liner covering said sealing surface of said cover and said opening in said cover, said liner being releasably sealed to said sealing surface of said cover by a second seal which is not subject to degradation by any ingredient contained in said reservoir; whereby ingredients contained in said reservoir are sealed therein during storage and non-use by said first and second seals, said cover and liner, but are free to flow through said opening and onto a subject's skin or mucosa when said liner is removed from said device and said device is applied to such skin or mucosa.

2. The device of claim 1, wherein said liner is a release liner for said device, said release liner covering said adhesive layer as well as said sealing surface and said opening of said cover.

3. The device of claim 2, wherein said first and second seals are heat seals between said cover and said backing member and between said liner and said cover respectively.

4. The device of claim 3 in which said liner is a composite member comprising:
    an outer protective layer and a barrier layer with an adhesive coating therebetween, and a release coating on the exposed surface of said barrier layer;
    said barrier layer, including its adhesive coating and its release coating, having an opening therein which is sufficiently large to expose said opening and said sealing surface of said cover, whereby said outer protective layer is sealed directly to said sealing surface of said cover by said second seal.

5. The device of claim 4 in which said adhesive layer is a composite member comprising:
    a first adhesive coating, a second adhesive coating and a barrier layer therebetween;
    said barrier layer, including its first adhesive coating and its second adhesive coating, having an opening therein which is sufficiently large to expose said opening and said sealing surface of said cover, whereby said outer protective layer is sealed directly to said sealing surface of said cover by said second seal.

6. The device of claim 5, wherein said release coating of said liner is releasably adhered to said second adhesive coating of said adhesive layer.

7. The device of claim 6, wherein said reservoir comprises an absorbable material.

8. The device of claim 7, wherein said topically active drug agent is salicylic acid.

9. The device of claim 8, wherein said salicylic acid is present in an amount of from about 5% to about 40% by weight of said organic solution.

10. The device of claim 9, wherein said alkylene glycol is propylene glycol.

11. The device of claim 10, wherein said fatty acid ester is glyceryl monoleate.

12. The device of claim 11, wherein said dialkylene glycol alkyl ether is diethylene glycol monoethyl ether.

* * * * *